United States Patent [19]

Childs, III

[11] Patent Number: 4,979,771
[45] Date of Patent: Dec. 25, 1990

[54] HAND TOOL FOR REMOVING TICKS FROM ANIMALS

[76] Inventor: Gordon E. Childs, III, 75 Grove Ave., Derby, Conn. 06418

[21] Appl. No.: 445,046

[22] Filed: Dec. 4, 1989

[51] Int. Cl.⁵ .......................... B25B 9/02; A61B 17/50
[52] U.S. Cl. .................................... 294/99.2; 606/51; 43/144
[58] Field of Search ..................... 294/99.2, 100, 902, 294/99.1; 128/399; 606/27–31, 131, 211, 51; 43/132.1, 134, 144; 219/227, 230

[56] References Cited

U.S. PATENT DOCUMENTS

| 201,916 | 4/1878 | Ensign | 43/134 |
| 3,214,210 | 10/1965 | Keirn | 294/99.2 |
| 3,980,861 | 9/1976 | Fukunaga | 294/99.2 X |
| 4,213,460 | 7/1980 | Weiner | 43/144 X |
| 4,303,268 | 12/1981 | Davidson | 294/100 X |
| 4,442,837 | 4/1984 | Keatley | 294/100 X |
| 4,662,068 | 5/1987 | Polonsky | 606/28 X |

FOREIGN PATENT DOCUMENTS 401328  2/1974  U.S.S.R. ................ 43/144

Primary Examiner—Margaret A. Focarino
Assistant Examiner—Dean J. Kramer

[57] ABSTRACT

A hand tool for removing ticks from the skin of a live animal. The tool includes two elongated arms having free ends shaped as hollow cup elements. When the two arms are squeezed toward each other the two cup elements cooperatively encircle the body of a tick protruding from the animal surface. Electrical heater elements within the cup elements apply heat to the tick body, causing the tick to loosen its hold on the animal skin. The tool can then be moved to lift the tick away from the animal skin surface.

1 Claim, 1 Drawing Sheet

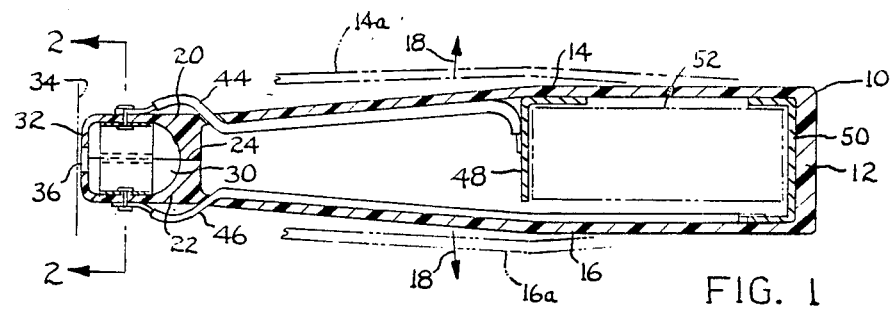
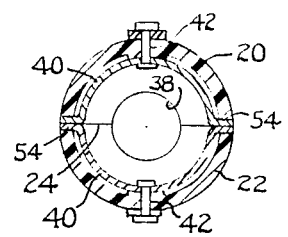
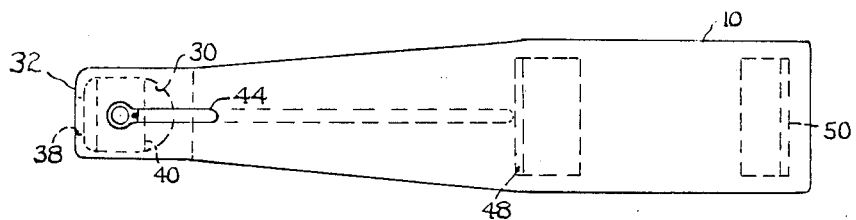

HAND TOOL FOR REMOVING TICKS FROM ANIMALS

BACKGROUND AND SUMMARY OF THE INVENTION

This invention relates to a hand tool especially adapted for removal of ticks from the skins of live animals, e.g. dogs.

Hand tools for a similar purpose are shown in U.S. Pat. No. 4,303,268 to H. Davidson and U.S. Pat. No. 4,442,837 to L. Keatley. The tools shown in those patents are in the nature of tweezers that have gripper jaws designed to engage side surfaces of the body of a tick partially embedded in the skin of a live animal. The tweezers are manually rotated around an axis normal to the skin surface to twist the tick body. Apparently the twisting action causes the tick to loosen its hold on the animal's skin.

The present invention contemplates a hand tool having a pair of opposed jaws configured as hollow cup sections. The cup sections can close around the body of a tick without actually applying any pressure on the tick body surfaces. Electric heater elements in each hollow cup section radiate heat onto (into) the tick body, such that the tick is caused to loosen its hold on the skin of the animal. The tool can then be moved away from the animal's skin surface to lift the tick from the animal surface. The tool has been found to be capable of removing the tick intact, without leaving the head embedded in the animal skin. The tool is easily operated, without any need for twisting the tool to loosen the tick from the animal's skin.

THE DRAWINGS

FIG. 1 is a sectional view through a hand tool embodying my invention.

FIG. 2 is a transverse sectional view taken on line 2—2 in FIG. 1.

FIG. 3 is a top plan view of the FIG. 1 tool.

DESCRIPTION OF A PREFERRED EMBODIMENT OF THE INVENTION

The tool shown in the drawing comprises a generally U-shaped tweezer structure 10 formed of a plastic material having resilient properties. The structure includes a web wall 12 and two longitudinal extending arms 14 and 16. Each arm can swing outwardly around its connection point with web wall 12, as indicated by arrows 18 in FIG. 1.

In FIG. 1 the two resilient arms 14 and 16 are shown in their squeezed-closed conditions. Removal of the manual squeeze force allows the arms to automatically open to the dashed line positions 14a and 16a.

The free ends of arms 14 and 16 are configured as hollow cup-shaped elements 20 and 22. Each cup element has an essentially flat circumferential edge 24. In the closed condition of FIG. 1 the two circumferential edges 24 mate (meet) together so that the two cup elements circumscribe an essentially closed interior space designated by numeral 30. When arms 14 and 16 spring open to their dashed line positions 14a and 16a the cup elements 20 and 22 separate.

Each cup element 20 or 22 has an external end surface 32 adapted to contact the skin of an animal. Numeral 34 in FIG. 1 illustrates the animal skin surface. A semi-circular notch 36 is formed in the circumferential edge 24 of each cup element at the associated end surface 32. The two notches 36 cooperatively form a circular opening 38 (FIG. 2) that is adapted to encircle the head of a tick embedded into the animal skin surface. The exposed body of the tick will be located within space 30 circumscribed by the two cup elements 20 and 22. Circular opening 38 is made to be slightly larger than the head of a tick so that the tick head will not be crushed when the two cup elements close together, as shown in FIG. 1.

An electrical resistance heater element 40 is mounted within each cup element 20 and 22. As seen in FIG. 2, each heater element is configured as a semi-circular band secured to the associated cup element wall by means of a rivet 42. The rivet forms an electrical connection between the associated heater element and an electrical lead wire 44 or 46. Lead wire 44 extends through a hole in arm 14 and then over to a metallic contact arm 48. Lead wire 46 extends through a hole in arm 16 and then over to a metallic contact arm 50. The two contact arms 48 and 50 are adapted to receive therebetween a dry cell battery 52. Alternatively, lead wires 44 and 46 could be connected to a household current source via an electrical plug, not shown.

The opposite ends of each heater element 40 are turned outwardly, as at 54, to form confronting contact surfaces; outturned ends 54 will be located in notches in cup edges 24. When arms 14 and 16 are squeezed together the confronting surfaces of outturned ends 54 make electrical contact to energize the heater elements. When the squeeze pressure is removed from arms 14 and 16 the contact surfaces 54 separate to break the electrical circuit.

Heater elements 40 are located on the inner surfaces of cup elements 20 and 22, such that the generated heat is radiated into circumscribed space 30 rather than outwardly through the cup element walls. The cup elements are formed of a dielectric material that has some thermal insulating properties.

The heat output from heater elements 40 tends to be concentrated at the center of the circumscribed space 30. The body of a tick located within space 30 will receive the heat, such that the tick will quickly loosen its hold on the animal skin surface. The hand tool can then be manipulated to lift the tick from the animal surface, with the head and body of the tick intact (connected). The hand tool can be operated with one hand, leaving the other hand free to hold the animal.

The drawings necessarily show a specific form that the invention can take. The invention can be practiced in other forms.

What is claimed is:

1. A hand tool for removing ticks from the skins of live animals, comprising:
   a pair of elongated swingably-connected arms (14, 16) having free ends, and opposed hand grip sections adapted to be manually squeezed to bring the free ends together;
   the free ends of said arms being configured as opposed hollow three dimensional cup sections (20, 22) adapted to cooperatively encircle the body of a tick protruding from the skin of an animal;
   each said cup section being formed of a dielectric material having thermal insulating properties, each cup section having an essentially flat circumferential edge (24) adapted to mate to a circumferential edge on the other cup section when the cup sections are brought together;

each cup section having an external end surface (32) adapted to contact the skin of an animal, and a notch (36) formed in the circumferential edge of each cup section at the associated end surface so that the two notches form a single opening adapted to cooperatively encircle a portion of a tick embedded in the animal's skin;

an electrical heater element mounted within each cup section to radiate heat onto an encircled tick; each heater element being configured as a semi-circular band extending along the interior surface of the associated cup section, with the plane of each semi-circle extending transverse to the length dimension of the associated arm (14, 16);

said semi-circular bands having confronting outturned edges (54) adapted to engage each other to complete an energizing circuit through the bands only when the cup sections are brought and means for supplying current to the semi-circular heating elements, said current supplying means comprising an electrical conductor extending along each elongated arm, onto an external surface of the associated cup section, and an electrical connection (42) between each conductor and the associated semi-circular band.

* * * * *